United States Patent [19]

Bos

[11] Patent Number: 5,475,123
[45] Date of Patent: Dec. 12, 1995

[54] POLYMERIC MATERIALS

[75] Inventor: Michael A. Bos, Pearcedale, Australia

[73] Assignees: Micronisers Pty. Ltd., Dandenong; Unilever Australia Limited, Port Melbourne, both of Australia

[21] Appl. No.: 64,167

[22] Filed: May 27, 1993

[30] Foreign Application Priority Data

Nov. 27, 1990 [AU] Australia .................................. PK3559
May 22, 1991 [AU] Australia .................................. PK6267

[51] Int. Cl.⁶ ...................................................... C07F 3/06
[52] U.S. Cl. ........................................................ 556/130
[58] Field of Search ............................................... 556/130

[56] References Cited

U.S. PATENT DOCUMENTS 3,859,236 1/1975 Blewett et al. ..................... 260/23 X
4,404,408 9/1983 Wirth et al. .............................. 568/680

FOREIGN PATENT DOCUMENTS 78032    7/1982  Australia .
62872    3/1987  Australia .
11009    7/1988  Australia .
0009000  8/1979  European Pat. Off. .
606736   1/1985  Japan .
60-6736  1/1985  Japan .
92348    5/1985  Japan .
27546    2/1988  Japan .
187996   3/1966  U.S.S.R. .
21116981 10/1983 United Kingdom .
09758    3/1989  WIPO .
89/09758 10/1989 WIPO .

OTHER PUBLICATIONS

Chemical Abstracts, vol. 68, No. 16, Apr. 15, 1968, 69948M.
Soviet rubber Technology 10, 38–39 (1967), Translation of: Kauchuk i Rezina 26 (1), 41–42 (1967).

*Primary Examiner*—Porfirio Nazario-Gonzales
*Attorney, Agent, or Firm*—Birch, Stewart, Kolasch & Birch

[57] ABSTRACT

A process for the preparation of a zinc-containing polymeric material which includes providing a divalent metal compound including zinc; a polyhydroxy compound; and a catalyst; mixing the divalent metal compound and the polyhydroxy compound in substantially stoichiometric amounts in the presence of the catalyst at a temperature sufficient to allow reaction therebetween; and isolating the polymeric material so formed.

15 Claims, No Drawings

POLYMERIC MATERIALS

This application is a request for U.S. examination under 35 U.S.C § 371 of International application No. PCT/AU91/00544, filed on Nov. 25, 1991.

The present application relates to a process the production of a polymeric material and uses for that material. In particular, the application relates to process for the production of a polymeric material form from a reaction between a metallic compound and polyhydroxy compound.

The interaction between single zinc containing compounds and polyhydroxy compounds such as propanetriol have been documented within the prior art, particularly materials formed by such a reaction, their properties and their application as pharmaceutical preparations and as additives to confer specific advantageous properties to various rubbers, organic polymers and resins.

Blewett et al in U.S. Pat. No. 3,859,23 describes the stabilisation of vinyl halide resin compositions with divalent metal propanetriolates, in particular, the stabilisation of vinylchloride polymers with a zinc compound. The zinc propanetriolate was prepared from zinc acetate and a large excess of glycerol by heating under nitrogen to 160° C. for 6 hours to give a yield of only 34% based on the zinc. Reaction at 220° C. gave quantitative yield. A similar reaction, using zinc carbonate at 200° C., afforded the product in 79% yield.

Taylor in United Kingdom Patent 2,101,132B (U.S. Pat. No. 4,544,761) describes a method for combining a zinc compound with propanetriol to afford a polymeric and plastic plate-like zinc-propanetriolate. The method of preparation of this polymer comprised mixing zinc oxide, or a zinc oxide forming material, with propanetriol in the proportion of about fifty parts by weight of zinc-containing compound to approximately 500 parts by weight of propanetriol, raising the temperature to about 260° C. and maintaining that temperature under constant stirring until added zinc oxide was predominantly converted to the propanetriolate, with evolution of water. The reaction was claimed to proceed at lower temperatures more slowly. The zinc-propanetriolate polymer had to be isolated from the large excess of glycerol by pouring the cooled mixture into water, filtering, washing and drying. The material has been shown to possess a layered structure by T. J. Hambly and M. R. Snow in Aust. J. Chem 36, 1249 (1983).

Taylor in U.S. Pat. No. 4,876,278 (PCT International Application WO 87/01281; AU86/00251; United Kingdom 2,191,941) describes pharmaceutical applications of zinc propanetriolate. He describes a method of applying the material through transdermal absorption. It is claimed to have fungicidal, antiarthritic, antimicrobial and bacteriostatic activity.

Taylor in Australian Patent 584,238 (PCT International Application WO 87/01379; AU86.00249) describes a modification of rubber and plastics by addition of the zinc-propanetriolate material prepared in a manner as described above in United Kingdom 2,101,132B during manufacture or processing, as well as controlling the addition and processing to selectively arrange the additive particles in the organic polymer, thereby improving either the tensile strength of the composite material or its resistance to deterioration by ultraviolet light.

In United States Patent 4,544,761, Taylor claims that the reaction between an excess of propanetriol and a zinc compound can occur at temperatures around 260° C. For example, propanetriol (5.4 mole) and zinc oxide (0.614 mole) were reacted together at 260° C. for 1 hour to afford a 90% yield of polymer. The reaction was also stated to be slow below a temperature of 210° C.

In U.S. Pat. No. 4,943,326, Taylor claims that crystalline zinc propanetriolate could be formed by subjecting a zinc oxide suspension in propanetriol to microwave irradiation. Although this technique involved a saving in time, the temperature for effective conversion was subsequently found to exceed 190° C. Again a large excess of glycerol was required.

As described in the prior art referred to above, complete reaction of a zinc compound such as zinc oxide only occurs with a large excess of polyhydroxy compound and only at relatively high temperatures of 190° C. to 220° C.

Accordingly it is an object of the present invention to overcome or at least alleviate one or more of these difficulties associated with the prior art.

Accordingly, in a first aspect of the present invention there is provided a process for the preparation of a zinc-containing polymeric material which includes providing
    a divalent metal compound including zinc;
    a polyhydroxy compound; and
    a catalyst;
mixing the divalent metal compound and the polyhydroxy compound in substantially stoichiometric amounts in the presence of the catalyst at a temperature sufficient to allow reaction therebetween; and isolating the polymeric material so formed.

It has been found that given appropriate reaction conditions, a substantially stoichiometric reaction at reduced temperatures can occur between a zinc compound and a polyhydroxy compound. The present invention resides in a process for the production of a polymeric material formed by the reaction of a zinc compound and a polyhydroxy compound wherein the process is performed in the presence of a catalyst. Preferably the process is performed at a temperature below the boiling point of the polyhydroxy compound. The process may be performed at a temperature of approximately 120° C. to 250° C., preferably approximately 120° C. to 180° C., most preferably approximately 120° C. to 150° C.

The term polyhydroxy compound as used herein refers to any organic compound having an availability of hydroxy groups, that is able to undergo a polymerisation reaction. Such a compound may be straight chained or branched, substituted or unsubstituted, the chain length preferably from $C_2$–$C_6$ having terminal hydroxy groups. Generally a polymerisation reaction with zinc oxide will be a dehydrogenation reaction.

Preferably, the polyhydroxy compound used in the process of the present invention is a triol, most preferably a propanetriol or a diol such as ethylene glycol, or glycerol.

The process may be performed with any source of zinc, which is able to react with a polyhydroxy compound. Such materials may be chosen from one or more of zinc metal, zinc oxide, carbonate, hydroxide acetate, benzoate and sulphide or any zinc salt which may decompose to the oxide on heating in air. The molar stoichiometry of reaction of the metallic compound to the polyhydroxy compound is preferably 1:1 but may range from 1:10 to 10:1.

As an option, zinc may be partially replaced by another suitable divalent element, resulting in a variation of the property of the polymeric composition. Other such elements include calcium, cobalt, boron, manganese, iron or copper or any such compound that is capable of forming a polymeric complex with a polyhydroxy compound.

Accordingly the divalent metal compound may be selected from any one or more of zinc oxide, zinc carbonate, hydroxide, zinc acetate, zinc benzoate and zinc sulphide optionally together with a calcium compound selected from any one or more of calcium oxide, calcium carbonate, calcium hydroxide, calcium acetate, and calcium benzoate.

The atomic ratio between the zinc and the other divalent metallic compound may range from approximately 1:1000 to 1000:1 preferably approximately 100:1 to 1:1 and most preferably approximately 5:1 to 1:1.

It has been found that the addition of an accelerator or a catalyst may increase the reaction rate at substantially lower temperatures than previously required. Whilst we do not wish to be restricted by theory, it is postulated that the role of the catalyst is to maintain a chemically active form of the zinc compound by continuously renewing its surface layer.

The catalyst is preferably an acid or acid salt, more preferably weak acid or a salt of a weak acid. Thus the catalyst may be a carboxylic acid. The catalyst may be selected from formic, acetic acid, propanoic, butyric, naphthenic, neo-decanoic, benzoic, caproic, citric lactic, oxalic, salicylic, stearic, tartaric, valeric acid, boric acid, trifluoroacetic acid or toluene 4-sulphonic acid or the like.

Alternatively, the catalyst may be chosen from the salts of these acids, such as zinc acetate, calcium acetate, zinc naphthenate, sodium acetate, potassium formate, zinc borate, or cadmium stearate. The ratio the catalyst to the zinc or other metal compound may be in the range 1:10,000 to 1:5 but most preferably in the range 1:50 to 1:10.

The reaction of equimolar portions of the polyhydroxy compound and the metallic compound may be performed in a wide variety of reactors, provided that there is good mixing of the components, by stirring, agitation or the like.

The reaction may be conducted in a mixer of the Z-arm type. A Sigma mixer may be used.

Alternatively, in a preferred aspect, the process of the present invention may be performed in a slurrying medium.

Accordingly, in a preferred aspect the process further includes providing a slurrying medium; and mixing the divalent metal compound, polyhydroxy compound and catalyst with the slurrying medium to form a slurry prior to reaction.

It has been found that relatively high yields may be achieved with substantially stoichiometric amounts of reactants if the process is performed in a suitable slurrying medium.

An appropriate slurrying medium is able to provide excellent mixing which promotes reaction of the components and heat transfer to or from the system. This slurrying medium may consist of a solvent or mixture of solvents which can be readily recovered unchanged at completion of the reaction. The slurrying medium may be chosen from any one or a combination of the following solvent types: monohydric alcohols, ethers, phthalate or other esters, glycol or polyoxo ethers or esters, sulphoxides, amides, hydrocarbons and partially or completely chlorinated or fluorinated hydrocarbons. In particular, commercial hydrocarbon boiling fractions, with flash points above 61° C., such as white spirit, Shellsol 2046™ or BP99L™.

Optionally, more than one type of slurrying medium may be employed. In particular, it is preferred that at least one of the components can be miscible with the polyhydroxy compound, such that at reaction temperature, a single liquid phase reaction medium is obtained for reaction with the zinc compound. Examples of a second solvent, miscible with propanetriol, are the monoalkyl ethers or esters of polyethylene glycol, such as diethylene glycol monobutyl ether and triethylene glycol monoacetate. If the optional second component is present, the ratio of the miscible component to the immiscible component is preferably 1:100 to 1:1 and most preferably 1:20 to 1:5.

The preferred polyhydroxy compound of choice for use in the process according to the invention is propanetriol. It will be useful by way of example to indicate preferred reaction conditions with a process involving this polyhydroxy compound. It should however be appreciated that this is not intended to be restrictive upon the scope of the present invention.

The ratio of slurrying medium to propanetriol should be adjusted to provide adequate slurry mobility under reaction conditions and can be in the range 1:10 to 10:1, preferably in the range 1:2 to 2:1. After completion of reaction, the slurrying medium is removed preferably by filtration or distillation or the like to leave a residue of zinc propanetriolate.

Optionally, traces of contaminants may be removed by further treating this material with water or other solvent, eliminating traces of soluble materials, and/or subjected to drying at elevated temperatures or reduced pressures eliminating volatile components.

In a preferred aspect the zinc-containing polymeric material is subjected to a size reduction step to reduce the particle size to less than approximately 25 micron, preferably less than approximately 20 micron, more preferably less than 17.5 micron.

Preferably the particle size is reduced such that at least 80% of the particles are of approximately 12.5 micron or less, preferably 9 micron or less.

The particle size of the zinc containing polymeric material may be reduced by a variety of techniques, such as, crushing, grinding, or milling, e.g. ball milling, attrition milling or jet milling.

Zinc propanetriolate for example is insoluble in all known common organic solvents. It is hydrolysed by water, dilute mineral acids and under alkaline conditions.

In a preferred embodiment of this aspect of the present invention the reaction may be performed using a steel belt plate or roller. As an example, a slurry of zinc oxide and glycerine stoichiometric ratio of approximately 1:1 is applied as a thin film to a heated drum. The plate or roller may be heated to a temperature of from 120° C. to 180° C. and maintained until reaction between approximately the zinc compound and the polyhydroxy compound is complete. Addition of a catalyst as described assists in achieving a lowering of the temperature sufficient to allow for completion of the reaction. The final product may be removed by a scraper blade and reduced by an appropriate method to achieve a suitable final product.

In a still further aspect of the present invention the polymeric material produced by the process of the present invention may be utilised as an additive in plastics materials, or included as an antibacterial, antimicrobial, bacteriostatic, antifungal, nematocidal or antifouling agent.

Accordingly the present invention provides a polymeric composition including an effective amount of at least one polymer; and a zinc-containing polymeric material having a particle size of less than approximately 25 micron preferably less than approximately 20 micron, more preferably less than 17.5 micron.

The zinc-containing polymeric material may be selected from zinc propanetriolate or zinc glycerolate and the like. The zinc-containing polymeric material may be of a suitable regular particle size. Preferably the particle size is such that at least 80% of the particles are of approximately 12.5 micron or less, preferably 9 micron or less.

The polymer may be an organic polymer. The organic polymer may be a synthetic or natural polymer.

The organic polymer may be selected from organic polymers and polymer blends chosen from the following types, polyethylene, polypropylene, polyvinyl chloride, polystyrene, polyacrylamide, polyester, polyamide or poly(acryonitrile-butadiene-sytrene). A polyolefin such as polypropylene is preferred. These polymers may then be processed into polymeric articles such as fibres, films, fabrics or coatings.

The zinc-containing polymeric material may be present in amounts of from approximately 0.01 to 20% by weight based on the total weight of the polymeric blend. The organic polymer may be present in amounts of approximately 80% to 99.99% by weight based on the total weight of the polymeric blend.

Accordingly, in a preferred aspect there is provided a polymeric composition including approximately 80 to 99.9% by weight based on the total weight of the polymeric composition of an organic polymer; and approximately 0.01 to 20% by weight based on the total weight of a zinc glycerolate or zinc propanetriolate having a particle size such that at least 80% of the particles are of approximately 12.5 micron or less.

Although zinc propanetriolate remains unchanged when incorporated into the polymer during processing (see Australian Patent 584,238 for characteristic XRD powder pattern), its incorporation into polymer products and subsequent hydrolysis leads to the disintegration of the polymer matrix in an aqueous environment.

The polymeric composition may further include conventional compounding ingredients in minor amounts. Compounding ingredients such as pigments, fillers, extenders, flow retardents, antioxidants, mould release agents, acid scavengers and the like may be incorporated into the polymeric composition.

Accordingly, in a further preferred aspect, there is provided a polymeric article formed from a polymeric composition including an effective amount of at least one polymer; and a zinc-containing polymeric material having a particle size of less than approximately 25 micron.

The polymeric article may be a film or fibre. The film or fibre has improved anti-bacterial properties and because of the hydrolysis of zinc propanetriolate is degradable in aqueous environment.

The polymeric composition may also be utilised in the formation of nappies, particularly disposable nappies. For example, zinc propanetriolate may be incorporated during the manufacture of polypropylene fibres, for use in the manufacture of nappies. In conjunction with its ability to assist in the breakdown of those fibres, the antibacterial and antimicrobial properties of the polymeric composition make in particularly suitable for use in the production of disposable nappies.

In a still further preferred aspect, there is provided a polymeric article, formed from a polymeric composition including approximately 80 to 99.9% by weight based on the total weight of the polymeric composition of an organic polymer; and approximately 0.01 to 20% by weight based on the total weight of a zinc glycerolate or zinc propanetriolate having a particle size such that at least 80% of the particles are of approximately 12.5 micron or less.

It has been found that the finely milled zinc-coating polymeric material, e.g. of zinc propanetriolate may function as a nucleating agent for polymers such as polyolefin homopolymers or copolymers and as a curing agent for, e.g. rubbers, during formation of the article.

It has been found that zinc propanetriolate for example incorporated into polymers such as polyolefin may accordingly increase the melt index or Tx value (crystallisation temperature) of the polymer. Preferably the rigidity of the article is increased by at least approximately 10% relative to the base organic polymer; and the crystallisation temperature is increased by at least approximately 10% relative to the base organic polymer.

The rigidity of the article may be increased by approximately 10 to 20% or even 30%. The clarity may also be improved for homopolymers and random copolymers by approximately 10 to 20%.

Testing on rubber compositions with finely milled zinc glycerolate which were compared to compounds with zinc oxide as a curing agent we found to have the following advantages:

(i) faster cure rate, (ii) improved compression set of approximately 20 to 30%, (iii) decrease in heat build-up approximately 3 to 7%, (iv) Use of zinc glycerolate effective at a level of approximately 40% by weight of the amount of e.g. zinc oxide needed to achieve an equivalent curing effect. Also the supplemental curing agent, stearic acid, is not required.

Preferably the base organic polymer utilised to form the polymeric article is selected from homopolymers or copolymers of aromatic or aliphatic polyolefins, vinyl polymers, acrylic polymers, polyesters, polyamides or rubbers. Polyolefins including homopolymers of copolymers of polyethylene and polypropylene are preferred. The polypropylene polymers sold under the trade designations HMA 6100, KMA 6100, HET 6100, PH 6100, KMT 6100 and available from Shell Chemicals have been found to be suitable. Rubbers such as natural rubber or acylonitrile-butadiene-styrene rubber are preferred.

Accordingly, there is further provided a process for the preparation of a polymeric article having increased rigidity which includes providing an effective amount of at least one organic polymer; and a zinc-containing polymeric material having a particle size of less than approximately 25 micron;

mixing the organic polymer and zinc-containing polymeric material; and forming the polymeric mixture into a desired shape at elevated temperature such that the zinc-containing polymeric material functions as a nucleating or curing agent.

Preferably the process includes providing approximately 80 to 99.9% by weight based on the total weight of the polymeric composition of an organic polymer; and approximately 0.01 to 20% by weight based on the total weight of a zinc glycerolate or zinc propanetriolate having a particle size such that at least 80% of the particles are of approximately 12.5 micron or less.

More preferably the polymeric article is formed by extrusion, injection moulding or calendering.

The formation step may be conducted at elevated temperatures, for example from approximately 120° C. to 250° C.

The present invention will be illustrated with reference to the following examples. It should be understood that these examples are merely illustrative of preferred embodiment of the invention and the scope should not be considered to be limited thereto.

EXAMPLE 1

Zinc oxide (81 Kg), glycerol (93 Kg) and zinc acetate dihydrate (2 Kg) as a catalyst was added to a mixture of the paraffinic solvent, BPl(50 L) and diethylene glycol monobutyl ether (2.5 L) in a 200 L reactor capable of being heated, vigorously stirred, and evacuated. The slurry was rapidly sitted, heated to 125° C. and kept at that temperature for 30 minutes during which time the reaction went to completion. Volatiles were removed under vacuum (20–25 in) at 125°–130° C. over the course of 1 hour, to afford a free flowing white powder of zinc-glycerol complex in quantitative yield. The complex was examined and showed an X-ray powder pattern characteristic of zinc propanetriolate (JCPDS file #23-1975). The material was analysed for zinc, which was found to be 44 wt %; the theoretical value expected for zinc propanetriolate was 42.06 wt %. This experiment shows that a large excess of glycerol is not necessary to manufacture the zinc-glycerol complex in quantitative yield.

EXAMPLE 2

The experiment in Example 1 was repeated, on 1/1000 scale, but with the omission of the zinc acetate catalyst. The reaction product was freed from unreacted glycerol by washing with water, then ethanol and drying in vacuum. The final white powder obtained exhibited an XRD powder pattern, characteristic of zinc oxide (JCPDS File #21-1486). This experiment shows that a temperature of 125° C. is insufficient to promote reaction between zinc oxide and glycerol in the absence of a catalyst.

EXAMPLE 3

The experiment in Example 2 was repeated, but with the omission of the diethylene glycol, monobutyl ether. Before reaction two phases were apparent, with the glycerol immiscible in the paraffin slurry medium. After completion of the reaction and product separation, the white powder obtained exhibited an XRD powder pattern, characteristic of a mixture of zinc oxide and zinc-glycerol complex. This experiment shows that, at a temperature of 125° C. in the presence of a zinc acetate catalyst, the reaction of zinc oxide and glycerol is incomplete if glycerol forms a separate liquid phase.

EXAMPLE 4

The experiment in Example 2 was repeated, but substituting glacial acetic acid (1 Kg), for zinc acetate. No unreacted zinc oxide was observed by XRD at the conclusion of the experiment. This example shows that the zinc acetate catalyst may be prepared in situ from reaction of zinc oxide and acetic acid.

EXAMPLE 5

The experiment in Example 2 was repeated, but substituting sodium benzoate (1 Kg), for zinc acetate. No unreacted zinc oxide was observed by XRD at the conclusion of the experiment. This example shows that other salts of acids may be used as a catalyst.

EXAMPLE 6

Zinc oxide (64.8 Kg), calcium oxide (11.2 Kg) glycerol (93 Kg) and zinc acetate dihydrate (2 Kg) as a catalyst was added to a mixture of the paraffinic solvent, BP 99 L (50 L) and diethylene glycol monobutyl ether, (2.5L) in a 200 L reactor capable of being heated, vigorously stirred, and evacuated. The slurry was rapidly stirred, heated to 125° C. and kept at that temperature for 30 minutes, during which time the reaction went to completion. Volatiles were removed under vacuum (20–25 in) at 125°–130° C. over the course of 1 hour, to afford a free flowing white powder of zinc-glycerol complex in quantitative yield. The complex gave a zinc analysis of 35.2 wt % and a calcium analysis of 5.4 wt %. This experiment shows that part of the zinc may be replaced by calcium to afford a mixed metal propanetriolate complex.

EXAMPLE 7

Glycerol (98 kg) is loaded into a stainless steel heated Z-arm (Sigma) mixer. Zinc oxide (75 kg), special grade 0.2 micron is added to the mixer and mixing begun. Zinc acetate dihydrate (0.5 kg) catalyst is added to the mixer and the mixture heated to 125° C. for approximately 30 minutes. A free-flowing white powder is formed in quantitative yield. In this example, elimination of volatiles is avoided.

Zinc glycerolate so prepared was then reduced in size by pin milling utilising an Alpine pin mill. Particles of 100 to 500 micron were reduced to a product in which of the particles were less than 12.5 micron in size.

EXAMPLE 8

Zinc propanetriolate (50 Kg), prepared as described in Example 1, was reduced in size by jet milling. Thus, by using an Alpine-202, jet mill of stainless steel construction, the following conditions were used to reduce 100–500 micron particles to a product in which more than 90% of the particles were less than 10 microns in size; grinding jet pressure=100 psi, feed rate=20–40 Kg/h, air temperature= 40°–100° C. and relative humidity=20–50%.

EXAMPLE 9

A mixture of zinc propanetriolate (20 Kg) sized as described in Example 7, and linear low density polyethylene (80 Kg) was mixed in a twin screw extruder and extruded at 220° C. to produce a masterbatch of polymer additive.

EXAMPLE 10

Test Specimen Preparation

Products with zinc glycerolate of particle size of less than 25 micron added were prepared by dry blending the additive to polypropylene nibs followed either by an extrusion step to yield a fully compounded pelletised product, or added directly to an injection moulding machine to fabricate the required test specimens.

Test specimen dimension and their preparation were performed according to the relevant physical test procedure.

Physical Testing (a) Flexural Modulus was performed according to ASTM D790.

(b) Melt Flow Rate (MFR) was determined according to ASTM D1238, 230° C., 2.16 kg.

(c) Falling Weight Impact Strength was determined according to BS2782:306B.

(d) Notched Izod impact strength was determined according to ASTM D256.

(e) Crystallisation temperature was determined using a Perkin Elmer Differential Scanning Calorimeter Model DSC-7 employing a 20° C./min cooling rate.

(f) Tensile Strength at Yield was determined according to ASTM D638.

(g) Long-term heat aging was carried out using an air-circulating oven set at 140° C.

(h) Clarity was measured using a Gardner Haze Meter System Model HG-1200 employing decalin as the reference medium.

Impact Heterophasic Copolymers

Impact Hetrophasic Copolymers of polypropylene possess ethylene weight fraction content ($E_t$) ranging from 4% to 25%, m/m. This ethylene is incorporated into the polymer structure as a finely dispersed, discreet process in secondary phase using an in-situ reactor contrast to post-reactor compounding process.

The effect of adding finely-milled zinc glycerolate at loadings up to 0.25%, m/m was investigated on a range of copolymers including Shell copolymer grades MA6100 (MFR=11 dg/min, $E_t$ range 5 to 12%, m/m), SMA6100 (MFR=4 dg/min, $E_t$ range 5 to 12$ m/m), SMD6100K (MFR=11 dg/min, $E_t$ range 15 to 25%, m/m).

The products with finely milled zinc glycerolate added possess greater flexural moduli (i.e. rigidity). This enhancement is generally in the range, 25 to 30% greater than the base polymer without additive.

Impact strength, measured by falling dart, was unaffected within experimental uncertainty. Notch impact strength is also little affected by the addition of Microstat 42.

Crystallisation temperature increased by 10 to 15% over that found for the base polymer (ca. 108° C.).

Homopolymers

Polypropylene homopolymer consists of polymer made solely of propylene monomer.

Similar loadings were investigated for Shell homopolymer grades including SM6100 (MFR=11 dg/min), VM5100K (MFR=23 dg/min), XY5900H (MFR=40 dg/min), JE6100 (2.5 dg/min).

The following changes to physical properties over the base polymer have been observed:

Flexural Modulus increased by 30 to 45%, Falling weight impact strength decreased by up to 75%, Crystallisation temperature increased by 20 to 25% (base polymer—ca.108° C.), Clarity is improved by 10 to 20%.

Results of oven testing showed no effect on long term heat stability (time for 100% of the samples show evidence of crazing), within experimental uncertainty, compared to the base polymer.

Random Copolymers

Random copolymers are made by incorporating monomer units of ethylene in the propylene polymer chain in a random fashion during the polymerisation process. This yields a product which is homogenous in nature in contrast to impact copolymers. The ethylene weight fraction content ($E_t$) may range from 0.5% to 10%, m/m.

Addition of 0.25%, m/m finely milled zinc glycerolate to Shell random copolymer grade HER6100 (MFR—1.5 dg/min, $E_t$ range of 1 to 6%, m/m) resulted in the following observations.

Flexural modulus increased by 25%, Falling weight impact strength was unaffected within experimental uncertainty, Crystallisation temperature increased by 15%, Clarity was improved by 25%.

EXAMPLE 11

Polypropylene polymers formed as in Example 10 were tested for improvement in crystallisation temperature. Results were compard with a similar polymer incorporating sodium benzoate as a nucleating agent. Results are set out in Table 1.

TABLE 1

| Additive | Amount (% by weight) | Crystallization temperature (Tx) |
|---|---|---|
| Sodium Benzoate | 0.25% | 109° C. |
| Zinc Glycerolate | 0.15% | 121° C. |
| Zinc Glycerolate | 0.25% | 127° C. |

EXAMPLE 12

Zinc oxide (81 g, 1.0 mol) and glycerol (101 g, 1.1 mol) were heated to 130°–140° C. in a beaker in the presence of trifluoroacetic acid (1 g) as catalyst for about 1 hour. On cooling the contents of the beaker were washed with ethanol (300 cm$^3$) filtered (sinter no. 3) and dried at 80° C. in an oven to give a yield of 108 g of zinc glycerolate. The infrared spectrum showed the following absorption bands (cm$^{-1}$): 3400, 7930, 2880, 2745, 2715, 2580, 2500, 1930, 1460, 1438, 1380, 1365, 1350, 1275, 1235, 1120, 1080, 1060, 990, 908, 875, 650. The absorption band at 7580 cm$^{-1}$ is attributed to a hydrogen bonded to oxygen in these glycerolate compounds (Radoslovich E. W., et al, Aust. J. Chem. 1970, 23, 1963).

EXAMPLE 13

Zinc oxide (40.5 g, 0.5 mol) and glycerol (51 g, 0.55 mol) were heated to 130° C. to 140° C. in a beaker in the presence of toluene-4-sulphonic acid (0.5 g) for about 1 hour. On cooling, the reaction mixture was dispersed in an ethanol/water (1:1) solvent, filtered (sinter no. 3) and finally washed with neat ethanol. After drying the white powder at 80° C. a yield of 36 g was obtained. The infrared spectrum was typical of zinc glycerolate and identical to that described in the previous example.

EXAMPLE 14

Rubber compositions were prepared in accordance with the following formulations as per ASTM D3184-88:

|  | Control Formulations (Parts by weight) | | |
|---|---|---|---|
| Black Mix | 1 | 2 | 3 |
| Natural rubber | 100.00 | 100.00 | 100.00 |
| Zinc oxide | 5.0 | 2.5 | 1.0 |
| Sulphur | 3.5 | 3.5 | 3.5 |
| Strearic acid | 0.5 | 0.5 | 0.5 |
| Oil furnace black | 35.0 | 35.0 | 35.0 |
| TBBS* | 0.7 | 0.7 | 0.7 |

Substituting finely milled zinc glycerolate for zinc oxide.

|  | Formulations (Parts by weight) | | |
|---|---|---|---|
| Black Mix | 1 | 2 | 3 |
| Natural rubber | 100.00 | 100.00 | 100.00 |
| Zinc glycerolate | 2.5 | 1.25 | 1.0 |
| Sulphur | 3.5 | 3.5 | 3.5 |

-continued

| | | | |
|---|---|---|---|
| Oil furnace black | 35.00 | 35.00 | 35.00 |
| TBBS* (n-tert-butyl-2-benzothiazolesulfenamide) | 0.7 | 0.7 | 0.7 |

3 sets of each

| | Control Formulations (Parts by weight) | | |
|---|---|---|---|
| IA Gum Mix | 1 | 2 | 3 |
| Natural rubber | 100.00 | 100.00 | 100.00 |
| Zinc oxide | 6.0 | 4.0 | 2.0 |
| Sulphur | 3.5 | 3.5 | 3.5 |
| Stearic acid | 0.5 | 0.5 | 0.5 |
| Mercaptobenzothiazole | 0.5 | 0.5 | 0.5 |

Substituting finely milled zinc glycerolate for zinc oxide.

| | Formulations (Parts by weight) | | |
|---|---|---|---|
| IA Gum Mix | 1 | 2 | 3 |
| Natural rubber | 100.00 | 100.00 | 100.00 |
| Zinc glycerolate | 3.0 | 1.5 | 1.0 |
| Sulphur | 3.5 | 3.5 | 3.5 |
| Mercaptobenzothiazole | 0.5 | 0.5 | 0.5 |

3 sets of each

Materials were compounded on a standard two roll rubber mill and standard miniotinic internal mixer as per ASTM mixing procedure D3182-87.
First Stage Masterbatch
  Rubber
  Stearic acid, zinc oxide or zinc glycerolate
  Dump
Second Stage Compound
  Masterbatch
  Curatives
  Dump
Test procedures were as per ASTM D3185-87

Testing on compounds with finely milled zinc glycerolate which were compared to compounds with zinc oxide as a curing agent we found to have the following advantages:

(i) faster cure rate, (ii) improved compression set of approximately 20 to 30%, (iii) decrease in heat build-up approximately 3 to 7%, (iv) Use of zinc glycerolate effective at a level of approximately 40% by weight of the amount of e.g. zinc oxide needed to achieve an equivalent curing effect. Also the supplemental curing agent, stearic acid, is not required.

Finally, it is to be understood that various other modifications and/or alterations may be made without departing from the spirit of the present invention as outlined herein.

I claim:

1. A process for the preparation of a zinc-containing material, which comprises providing
   a divalent metal compound including zinc;
   a polyhydroxy compound; and
   a catalyst;
   mixing the divalent metal compound and the polyhydroxy compound in substantially stoichiometric amounts in the presence of the catalyst at a temperature sufficient to allow reaction therebetween; and
   isolating the material so formed;
   wherein said catalyst is an acid or a salt thereof.

2. The process according to claim 1, wherein the reaction temperature is in the range of approximately 120° C. to 180° C.

3. The process according to claim 2, wherein the divalent metal compound is selected from one or more of zinc oxide, zinc carbonate, zinc hydroxide, zinc acetate, zinc benzoate and zinc sulphide optionally together with a calcium compound selected from one or more of calcium oxide, calcium carbonate, calcium hydroxide, calcium acetate, and calcium benzoate.

4. The process according to claim 3, wherein the polyhydroxy compound is selected from organic diols and triols.

5. The process according to claim 4, wherein the polyhydroxy compound is glycerol or propanetriol.

6. The process according to claim 5, wherein the catalyst is selected from formic acid, acetic acid, propanoic acid, butyric acid, naphthenic acid, neodecanoic acid, benzoic acid, caproic acid, citric acid, lactic acid, oxalic acid, salicylic acid, stearic acid, tartaric acid, valeric acid, boric acid, trifluoroacetic acid and toluene 4-sulphonic acid.

7. The process according to claim 1, which further comprises
   mixing the divalent metal compound, polyhydroxy compound and catalyst with a slurrying medium to form a slurry prior to reaction;
   wherein said slurrying medium is selected from one or more of monohydric alcohols, ethers, esters, glycol or polyoxo ethers or esters, sulphoxides, amides, hydrocarbons and partially or completely chlorinated or fluorinated hydrocarbons.

8. The process according to claim 1, which further comprises subjecting the zinc-containing material to a size reduction step to reduce the particle size to less than approximately 25 microns.

9. The process according to claim 8, wherein said size reduction step is carried out by subjecting the material to a milling step.

10. The process according to claim 2, wherein said reaction temperature is in the range of about 120° C. to 150° C.

11. The process according to claim 1, wherein the catalyst is present, based on the amount of metal compound, in a ratio ranging from 1:50 to 1:10, respectively.

12. A process, which comprises:
   mixing a divalent zinc-containing metal compound and a polyhydroxy compound in substantially stoichiometric amounts; and
   reacting, in the presence of a catalyst, said metal compound with said polyhydroxy compound to thereby form a solid zinc-containing material;
   wherein said catalyst is an acid, or a salt thereof.

13. The process according to claim 12, which further comprises:
   isolating said solid zinc-containing material; and
   forming the zinc-containing material into particles having a particle size of less than about 20 microns.

14. The process according to claim 12, wherein said reaction is carried out in a slurry.

15. The process according to claim 14, wherein said mixing step comprises mixing together said metal compound, said polyhydroxy compound, said catalyst, and a slurrying medium.

* * * * *

UNITED STATES PATENT AND TRADEMARK OFFICE
CERTIFICATE OF CORRECTION

PATENT NO. : 5,475,123
DATED : Dec. 12, 1995
INVENTOR(S) : Bos

It is certified that error appears in the above-indentified patent and that said Letters Patent is hereby corrected as shown below:

On the title page, before item [30] insert the following:
Related U.S. Application Data
--[63] Continuation of PCT/AU91/00544, filed Nov. 25, 1991.--.

Signed and Sealed this

Thirteenth Day of August, 1996

Attest:

BRUCE LEHMAN

*Attesting Officer*     Commissioner of Patents and Trademarks